United States Patent [19]

Norman et al.

[11] Patent Number: 5,085,731

[45] Date of Patent: Feb. 4, 1992

[54] VOLATILE LIQUID PRECURSORS FOR THE CHEMICAL VAPOR DEPOSITION OF COPPER

[75] Inventors: John A. T. Norman, Whitehall; Beth A. Muratore, Elverson, both of Pa.

[73] Assignee: Air Products and Chemicals, Inc., Allentown, Pa.

[21] Appl. No.: 650,332

[22] Filed: Feb. 4, 1991

[51] Int. Cl.$^5$ .................. C23C 16/14; B44C 1/22; C03C 15/00

[52] U.S. Cl. ........................ 156/646; 156/654; 156/655; 156/656; 156/666; 427/250; 427/252; 427/253; 427/255.1

[58] Field of Search ............ 427/250, 252, 253, 255.1; 156/646, 654, 655, 656, 666

[56] References Cited

U.S. PATENT DOCUMENTS

| | | |
|---|---|---|
| 2,704,727 | 3/1955 | Pawlyk .................. 427/252 |
| 2,704,728 | 3/1955 | Pawlyk .................. 427/252 |
| 4,842,891 | 6/1989 | Miyazaki et al. ........... 427/252 |
| 4,948,623 | 8/1990 | Beach et al. .............. 427/252 |

Primary Examiner—Shrive Beck
Assistant Examiner—Margaret Burke
Attorney, Agent, or Firm—Mark L. Rodgers; William F. Marsh; James C. Simmons

[57] ABSTRACT

Volatile liquid organometallic copper complexes are provided which are capable of selectively depositing a copper film onto metallic or other electrically conducting portions of a substrate surface under CVD conditions. These organometallic copper complexes are represented by the structural formula:

$$Cu^{+1}(R^1-\underset{\underset{O}{\|}}{C}-\underset{\underset{R^2}{|}}{C}-\underset{\underset{O}{\|}}{C}-R^3)^{-1}\cdot C(R^4)(R^5)=C(R^5)Si(R^6)_3$$

wherein $R^1$ and $R^3$ are each independently $C_1$-$C_8$ perfluoroalkyl, $R^2$ is H, F or $C_1$-$C_8$ perfluoroalkyl, $R^4$ is H, $C_1$-$C_8$ alkyl, or $Si(R^6)_3$, each $R^5$ is independently H or $C_1$-$C_8$ alkyl and each $R^6$ is independently phenyl or $C_1$-$C_8$ alkyl. A process for depositing copper films using these organometallic copper complexes is also provided.

11 Claims, No Drawings

VOLATILE LIQUID PRECURSORS FOR THE CHEMICAL VAPOR DEPOSITION OF COPPER

TECHNICAL FIELD OF THE INVENTION

The present invention relates to complexes useful for the deposition of copper films onto conducting metallic or metallic-like surfaces.

BACKGROUND OF THE INVENTION

In the electronics industry there is a steady trend towards manufacturing microprocessors of increasingly high speed and large information storage capacity. This requires the individual electrical devices such as transistors, etc. within the microprocessors to be fabricated at an increasingly small scale. The metallic electrical interconnects between the devices also need to be miniaturized. As device and interconnect dimensions approach one-half to one-quarter of a micron, the choice of interconnect metal becomes critical. The large current densities resulting from small interconnect cross sectional areas can lead to major problems such as electromigration, stress migration, and voiding where the metal lines become fractured or otherwise physically degraded under operating conditions, a major drawback with aluminum alloys. Metal interconnects also need to provide the lowest electrical resistance path possible since resistance-capacitance delays become a dominant factor in circuit performance at sub half micron levels. The aluminum that is widely used in present day interconnect manufacturing is reasonably conductive (2.7 microohm cm), but needs to be alloyed with 0.5 to 4.0% Cu to minimize the electromigration tendencies of the pure metal. Tungsten, also widely used, is electromigration resistant but is of higher resistivity (5.4 microohm cm). Considering these facts, copper should be an excellent interconnect metal as it is both highly conductive (1.7 microohm cm) and electromigration resistant.

Metallic interconnects are typically horizontal lines (runners) or plugs (vias) that wire together devices in microprocessors. At feature sizes of >1 micron these metallic components can be built into the microcircuits by PVD (Physical Vapor Deposition) techniques such as sputtering or evaporation. In essence PVD consists of condensing a metal vapor onto a surface or into a hole or channel of a circuit where an electrical connection needs to be formed. Since this is a non-selective metallization, either a postdeposition clean-up (i.e. etchback) or a predepositon masking of the substrate (i.e. the lift-off technique) is required in order to prepare individual discreet metal components. However, the severe surface topographies presented by sub-micron features preclude the effective use of PVD since this "line of sight" technique cannot provide a uniform conformal coating on such high aspect ratio highly convoluted surfaces. Specific examples of these shortcomings include the phenomena of geometrical shadowing and poor step coverage.

A superior process for producing these microscopic metal features is CVD (Chemical Vapor Deposition). In this technique a volatile metal-organic compound in the gas phase is contacted with areas of a circuit where growth of a metal film (i.e. interconnect) is required. A surface catalyzed chemical reaction then occurs which leads to deposition of the desired metal. Since this is a chemical reaction, there is potential for it to provide surface selective metallization. That is, CVD metal deposition can be made to occur at only specific locations compared to the non-selective PVD processes. Also, since the metal film steadily grows on the desired surface it is of a uniform thickness and highly conformal even to severe geometries. In this respect CVD is naturally suited to fabricating submicron high aspect ratio features.

An example of selective CVD metallization that is currently commercially practiced is the deposition of tungsten onto a silicon surface using tungsten hexafluoride as the volatile organometallic precursor (see T. Ohba, et al., "Tungsten and Other Advanced Metals for VLSI/ULSI Applications V," Ed. by S. S. Wong and S. Furukawa, MRS, Pittsburgh, Pa. 273 (1990)). The chemistry that drives this process can be divided into two steps. Initially the $WF_6$ reacts with the elemental silicon surface to yield tungsten metal and volatile silicon hexafluoride. Hydrogen gas is then added to the system which reduces further $WF_6$ at the freshly formed metal surface thereby yielding additional tungsten and HF gas. Although this system currently enjoys widespread use as the only "selective" CVD metallization process that is widely commercially available, loss of selectivity can be observed and is commonly ascribed to the corrosive nature of HF. . Ohba, et al., Tech Dig. IEDM, 213 (1987) teach the use of silane as a reducing agent for $WF_6$ to achieve higher deposition rates while avoiding the production of HF gas.

Desirable selectivities for a copper CVD process include deposition onto conducting metallic or metallic like surfaces such as tungsten, tantalum, titanium nitride or platinum silicide versus insulating surfaces such as silicon oxide. These metallic surfaces provide a diffusion barrier between the CVD copper and the underlying silicon substrate that the device is grown upon.

Copper films have previously been prepared via CVD using various copper presursors. Most of these compounds will only deposit copper metal at temperatures higher than 200° C. with significant selectivity between substrates such as diffusion barrier surfaces vs. silicon oxide. The best known and most frequently used CVD copper precursor is the solid compound copper$^{+2}$ bis(hexafluoroacetylacetonate). This highly fluorinated organometallic precursor is significantly more volatile than its parent unfluorinated complex copper$^{+2}$ bis(acetylacetonate) and its ease of vaporization readily lends this compound towards CVD processes. The use of this compound as a general precursor for CVD copper metallization was first described by F. L. Van Hemert et al. *J. Electrochem. Soc.* (112), 1123 (1965) and by R. W. Moshier et al. U.S. Pat. No. 3,356,527. More recently Reisman, et al., *J. Electrochemical Soc.*, Vol. 136, No. 11, November 1989 and A. E. Kaloyeros et al., *Journal of Electronic Materials,* Vol. 19, No. 3, 271 (1990) in two independent studies have also evaluated the use of this compound as a copper precursor for electronics applications. In these studies copper films were formed by contacting vapors of copper$^{+2}$(hfac)$_2$, mixed with either an inert gas (argon) or with hydrogen and contacting the mixture with a heated substrate surface. In the case of using hydrogen the copper$^{+2}$ atom in the precursor complex is formally reduced to copper metal while the hfac$^{-1}$ ligand becomes protonated to yield a neutral volatile compound. In the case of using an inert gas the copper$^{+2}$(hfac)$_2$ is simply pyrolyzed to give copper metal and fragments of the hfac ligand.

Pure copper is reported for the hydrogen reduction but oxygen and carbon are found in the films obtained by pyrolysis. However, the lowest deposition temperatures for either process is 250° C. and no strong selectivities towards metallic vs. silicon oxide surfaces are reported. Copper films have also been prepared from copper$^{+2}$(hfac)$_2$ by plasma enhanced deposition, C. Oehg, M. Suhr, *Appl. Phy. A.* (45) 151-154 (1988), laser photothermal decomposition, F. A. Houle; C. R. Jones; T. Baum; C. Pico; C. A. Korae; *Appl. Phys. Lett.* (46) 204-206 (1985), and photochemical decomposition of copper$^{+2}$(hfac)$_2$ ethanol adducts, F. A. Houle; R. J. Wilson; T. H. Baum; *J. Vac. Sci. Technol. A* (4), 2452-2458 (1986). Some of these methods yield fluorine contaminated films and none are reported to yield selective depositions. Similar hydrogen reduction of volatile copper compounds has also been demonstrated by Charles et al. U.S. Pat. No. 3,594,216 using copper$^{+2}$ β-ketoimine complexes at 400° C. to deposit copper metal films onto glass or quartz substrates. No mention of selectivity is made. G. S. Girolami, et al., *Chem. Mater.* (1) 8-10 (1989) reported using solid copper$^{+1}$ t-butoxide to yield copper films by CVD at 400° C., but the resultant films were impure in that they contained 5% oxygen.

The only CVD precursors known to deposit pure copper metal films below 200° C. are the copper$^{+1}$ cyclopentadienyl phosphine compounds described by Beech et al., *Chem. Mater.* (2) 216-219 (1990), but these are also not reported to be strongly selective towards metallic or metallic like surfaces vs. silicon oxide or similar insulating dielectrics. An additional problem that this particular class of compounds faces for electronics applications is their potential to contaminate microcircuits with phosphorus, an element that is extensively used as a silicon dopant.

SUMMARY OF THE INVENTION

The present invention is a class of volatile liquid organometallic copper complexes which are capable of selectively depositing a copper film onto metallic or other electrically conducting portions of a substrate surface under CVD conditions. These organometallic copper complexes are represented by the structural formula:

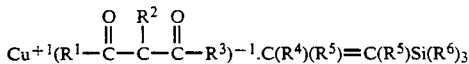

wherein $R^1$ and $R^3$ are each independently $C_1$-$C_8$ perfluoroalkyl, $R^2$ is H, F or $C_1$-$C_8$ perfluoroalkyl, $R^4$ is H, $C_1$-$C_8$ alkyl, or $Si(R^6)_3$, each $R^5$ is independently H or $C_1$-$C_8$ alkyl and each $R^6$ is independently phenyl or $C_1$-$C_8$ alkyl. Additionally, the present invention is also a CVD process for selectively depositing copper films using these organometallic copper complexes.

The above compounds have been found to be distillable liquids which exhibit excellent properties as CVD precursors; such as the ability to selectively deposit copper onto metallic or other electrically conducting portions of a substrate surface to the exclusion of deposition onto silicon oxide or other similar non-conducting (ie. insulating) surfaces, even at temperatures less than 200° C. Unlike typical prior art CVD copper precursors, the complexes of the present invention are liquid under ambient conditions which allows them to be utilized in standard "bubbler" precursor delivery systems that are widely used in the electronics industry.

Additionally, it has been found that the deposition reaction can be reversed to cleanly and selectively etch deposited copper from a substrate surface. In this process, a substrate on which has been deposited a copper film is contacted with an organometallic copper complex and an olefin, in the gas phase, represented by the structural formulae:

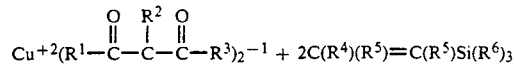

where $R^1$, $R^2$, $R^3$, $R^4$, $R^5$, and $R^6$ are the same as above.

DETAILED DESCRIPTION OF THE INVENTION

An improved class of CVD precursors has been developed which are capable of selectively depositing pure, thin copper films on metallic or other electrically conducting portions of a substrate surface. These precursors are organometallic copper complexes, and more specifically, copper$^{+1}$(β-diketonate)silylolefin complexes wherein the silylolefin is a stabilizing ligand composed in part of a silicon atom connected to an olefinic double bond. These organometallic copper complexes can be represented by the structural formula:

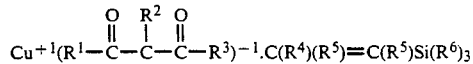

wherein $R^1$ and $R^3$ are each independently $C_1$-$C_8$ perfluoroalkyl, $R^2$ is H, F or $C_1$-$C_8$ perfluoroalkyl, $R^4$ is H, $C_1$-$C_8$ alkyl, or $Si(R^6)_3$, each $R^5$ is independently H or $C_1$-$C_8$ alkyl and each $R^6$ is independently phenyl or $C_1$-$C_8$ alkyl.

We have unexpectedly found these complexes to be distillable liquids at room temperature which exhibit excellent properties as CVD precursors for the selective deposition of copper onto metallic or other electrically conducting portions of a substrate surface while avoiding deposition on silicon oxide or other insulating (ie. non-conductive) portions of the surface. Such metallic or other electrically conducting surfaces include: W, TiN, Ta, Al, PtSi, and the like. The deposition conditions are those typically employed in conventional low pressure CVD applications, with the exception that, in additional to conventional CVD temperatures, the present process allows for substantially lower deposition temperatures to be used, ie., below 200° C., and in some instances, depending upon the specific complex used, temperatures as low as about 120° C. can be used.

While not intending to be bound by theory, it is believed that as CVD precursors, these compounds function by a surface catalyzed disproportionation to give a volatile Cu$^{+2}$ complex, free olefin and copper metal. For the precursors to be useful it is essential that the olefin is bound strongly enough to permit vaporization without extensive decomposition, yet weakly enough at elevated temperatures to permit disproportionation and copper deposition to occur, as in the CVD process. A possible mechanism is represented below for the volatile liquid complex copper$^{+1}$hfac.TMVS (hfac being an abbreviation for the hexafluoroacetylacetonate anion and TMVS being an abbreviation for trimethylvinylsilane). Both the TMVS and the Cu$^{+2}$(hfac)$_2$ are volatile byproducts; (s) denotes interaction with a surface and (g) denotes the gas phase.

$$2Cu^{+1}hfac.TMVS\ (g) \rightarrow 2Cu^{+1}hfac.TMVS(s) \quad \quad 1.$$

$$2Cu^{+1}hfac.TMVS\ (s) \rightarrow 2Cu^{+1}hfac(s) + 2TMVS\ (g) \quad \quad 2.$$

$$2Cu^{+1}hfac\ (s)\ Cu(s) + Cu^{+2}(hfac)_2(g) \quad \quad 3.$$

In step 1, the complex is adsorbed from the gas phase onto a metallic surface. In step 2. the coordinated olefin (TMVS in this specific case) dissociates from the complex as a free gas leaving behind $Cu^{+1}hfac$ as an unstable compound. In step 3, the $Cu^{+1}hfac$ disproportionates to yield copper metal and volatile $Cu^{+2}(hfac)_2$.

The disproportionation at CVD temperatures appears to be most strongly catalyzed by metallic or electrically conducting surfaces thereby providing the system with a selectivity that is very attractive from a microelectronics processing perspective.

The present organometallic complexes have the ability to selectively deposit copper films having small grain size even at low temperatures, i.e., from 120° to 200° C. without significantly compromising the growth rate of the film. The small grain size of the deposited metal minimizes the need for post deposition planarization. Additionally the ability to deposit copper at these lower temperatures is especially important for the so called upper-level metals in multi-metal layer ICs as excessive heat is to be avoided during the later stages of microprocessor fabrication to prevent thermally induced interdiffusion of layer materials and dopants at device interfaces. Also, since useful deposition rates, appropriate grain size etc. can be accomplished below 200° C. standard photoresist materials can be used for patterning purposes via photolithographic techniques. Also, as stated above, because these complexes are liquids under ambient conditions they can be utilized in standard CVD "bubbler" precursor delivery systems currently used in the electronics industry.

Additionally, the present process is advantageous in that it does not result in the release of corrosive or otherwise detrimental byproducts that can lead to a loss of selectivity or damage to the microprocessor substrate.

In an additional embodiment, hydrogen can be used in the CVD reduction of the organometallic copper complexes of the present invention to yield metallic copper in a similar manner that it is reported to reduce $Cu^{+2}(hfac)_2$. This more effectively utilizes the precursor from the perspective that each metal center would yield metallic copper in contrast to the disproportionation reaction where only ½ of the initial $Cu^{+1}$ centers yield copper metal. In instances in which this results in the loss of selectivity, an initial selective deposition in the absence of hydrogen can be utilized to deposit a seed layer of copper which would then be grown by subsequent CVD processing by hydrogen reduction. Optionally, other reducing gases could also be used.

It has also been found that the present CVD reaction could be reversed such that copper metal deposited via a blanket deposition reaction could be removed, i.e., etched from the metallic surface area of a substrate. In accordance with this technique, a copper (+2) complex along with a suitable silylolefin, both in the vapor phase, are brought into contact with a substrate onto which excess copper has been deposited. The copper metal on the surface of the substrate is converted into a volatile copper (+1) complex and is evaporated away from the metal surface. The general chemical equation for this etching reaction is as follows:

$$Cu^{\circ} + Cu^{+2}(ligand)_2 + 2\ silylolefin \rightarrow 2Cu^{+1}(ligand).silylolefin$$

Suitable ligands and silylolefins for this reaction correspond to those of the metal complex precursor set out above. Prior to the present invention, known etching processes were inappropriate for copper since prior processes resulted in the generation of copper halides which are involatile and were left behind as surface contaminants.

EXPERIMENTAL

Synthesis

The organometallic copper complexes of the present invention can be synthesized in accordance with the procedure described by Doyle in Organometallics, vol. 4, No. 5, 830 (1985), wherein an hfac ligand is reacted directly with cuprous oxide in THF under ambient conditions of temperature and pressure. This procedure is essentially an acid-base reaction that liberates water, and although Doyle states that the resulting complexes are water insensitive, we found this not to be the case. In the general course of our syntheses, and especially in the distillation of the TMVS complex, we found that disproportionation would occur to some extent unless water was rigorously excluded.

In order to overcome this detrimental effect of water on the resultant complexes, we have developed a process scheme which eliminates or greatly reduces the production of water. In this new synthesis technique, the potassium salt of hfac is reacted with cuprous chloride and the desired silylolefin in a suitable solvent media, such as THF or hexane. This new synthesis technique can be shown as follows:

$$K(hfac) + CuCl + olefin \xrightarrow{solvent} Cu\ hfac.olefin + KCl$$

For the copper chloride reactions 0.163 moles of cuprous chloride were stirred with 0.163 moles of potassium hfac [i.e. $K^+(hfac)^-$] along with 0.163 moles of olefin (for comparative purposes) or silylolefin in either 200 ml THF or hexane solvent for 18 hrs at room temperature under one atmosphere of nitrogen. The reaction mixture was then filtered and solvent stripped from the filtrate. A sample of the resultant crude reaction mixture was then submitted for $^1H$ NMR analysis. An attempt was then made to distill the crude product if it was found to be a liquid or to sublime it if it was found to be a solid. Any distillate or sublimate recovered from this procedure was also submitted for $^1H$ NMR analysis, as was any involatile residue. Typically $Cu^{+2}(hfac)_2$ was liberated from many of these sublimation/distillations and was identified by infrared spectroscopy.

For the copper oxide reactions 0.014 moles of cuprous oxide were stirred with 0.028 moles of hfac in the presence of 0.028 moles of olefin or silylolefin in 100 ml of THF solvent under one atmosphere of nitrogen for 18 hrs at room temperature. These reactions were then worked up and evaluated as above for the cuprous chloride reactions. Only the silylolefin based syntheses, with the exception of the 1-tridecene preparation, yielded any stable liquid complexes.

The potassium hfac used in the THF reactions was prepared by digesting 0.163 moles of potassium hydride in 100 ml of THF at room temperature under an atmosphere of nitrogen by the slow addition with stirring of 0.163 moles of hexafluoroacetylacetone followed by a period of further stirring until all H₂ evolution had ceased. Stripping off the THF solvent by vacuum provided the solid potassium hfac used in the hexane reaction.

Reaction product analysis was primarily by NMR. Since vinylic protons experience an NMR upfield chemical shift upon coordination to $Cu^{+1}$ [13] we were able to obtain a general indication as to whether the desired complexes had formed or not by measuring the chemical shift of olefinic protons present in reaction products. If a complex appeared to have formed by NMR an attempt was made to sublime it. As a further check, even reactions that appeared to be unsuccessful by NMR were subjected to a trial sublimation in an attempt to liberate any traces of the desired complex that might be present. These sublimation tests were also conducted to estimate the potential of a given complex as a CVD precursor by simply testing if it could form a chemically stable vapor. Pure $Cu^{+1}$hfac.olefin and silyl olefin complexes are bright yellow. In general, if a reaction turned green or blue from the generation of $Cu^{+2}(hfac)_2$ and/or generated metallic copper this was taken as an indicator that disproportionation had occured, in turn reflecting the synthesis of an unstable transient copper$^{+1}$ complex. This was especially true for the non-oxide reactions where water was absent from the reaction mixture, thereby eliminating it as a a potential destabilizer of what otherwise might have been a stable complex.

EXAMPLES

In the following examples, temperatures are set forth uncorrected in degrees celcius. Unless otherwise noted, all parts and percentages are by weight. 1,1.1,5,5,5-hexafluoro-2,4-pentanedione was purchased from Fairfield Chemical Company, Blythewood, S.C. Trimethylvinylsilane, 3.3-dimethyl-1-butene, 1-tridecene. 1-hexene and potassium hydride were purchased from Aldrich Chemical Co.. Milwaukee Wis. 4,4-dimethyl-1-pentene was purchased from Fluka Chemical Corp., Ronkonkoma, N.Y. Copper$^{+1}$ oxide and copper$^{+1}$ chloride were purchased from Aldrich, the latter reagent purified prior to use by the procedure described in *Inorganic Synthesis* Vol 2, p.1. Diethylmethylvinylsilane was purchased from Huls. Piscataway. N.J. HPLC grade terahydrofuran (THF) and HPLC grade hexane were distilled from sodium benzophenone under an atmosphere of nitrogen prior prior to use. All operations in the preparation of metal complexes were carried out using standard Schlenk line techniques as described by D. F. Shriver in the "Manipulations of Air Sensitive Compounds" McGraw-Hill Publishing Co. $^1H$ $^{13}C$ and $^{19}F$ NMR were recorded using Bruker ACP-300 and SY-200 spectrometers.

EXAMPLE 1

Runs were carried out to synthesize $Cu^{+1}$hfac.TMVS using both the synthesis described above (using CuCl) and that described by Doyle (using Cu₂O). Reacting potassium hfac with cuprous chloride and TMVS in hexane over an 18 hour period at room temperature yielded a bright yellow solution and a pale brown precipitate. Filtration and evaporation of hexane via vacuum produced a golden colored oil which was then purified by bulb to bulb vacuum distillation at 50 mtorr by heating to crude product to 50° C. and cooling the collection bulb to 0° C. After repeating this process on the distillate the resulting product (60% yield) could then be fractionally vacuum distilled to yield a pure bright yellow liquid complex. By reacting potassium hfac with cuprous chloride and TMVS in THF the same volatile liquid complex was isolated, but at a lower yield. By reacting H(hfac)ligand with cuprous oxide and TMVS in THF again yielded the same complex, but contaminated with $Cu^{+2}(hfac)_2$. Since water is generated in this oxide reaction, the observed disproportionation to give $Cu^{+2}(hfac)_2$ is consistent with our discovery that water destabilizes these complexes. In the first two reactions above no $Cu^{+2}(hfac)_2$ or copper metal contamination was observed in the reaction solutions. The analytical results of the run using cuprous chloride in hexane are as follows:

$Cu^{+1}(hfac).TMVS$: 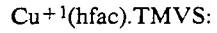
Yield = 60%
$^1H$ NMR (deuterobenzene): δ0.0 (s.9H); δ4.07 (m,3H), δ6.17 (s,1H)
$^{13}C$ NMR{deuterobenzene): δ−2.0 (s,1C); δ89 (s,1C); δ90 (s,1C); δ100 (s,1C); δ118 (q,2C); δ179 (q,2C)
$^{19}F$ NMR(deuterobenzene): δ−76 (s,6F)

EXAMPLE 2

A run was carried out wherein diethylmethylvinylsilane (DEMVS) was substituted for TMVS in the TMVS/CuCl/K⁺(hfac)⁻/hexane reaction described above resulting in the isolation of $Cu^{+1}$hfac.DEMVS complex as a volatile liquid in 51% yield. No $Cu^{+2}(hfac)_2$ or copper metal was observed in the reaction solutions. The analytical results of this run are as follows:

$Cu^{+1}(hfac).DEMVS$ 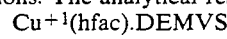
Yield = 51%
$^1H$ NMR (deuterobenzene): δ0.0 (s,9H); δ0.50 (q,4H); δ0.9 (t,6H); δ4.2 (m,3H); δ6.25 (s,1H)
$^{13}C$ NMR (deuterobenzene): δ−4.5(s,1C), δ7.0 (s,2C); δ8.5 (s,2C) δ91.6 (s,1C; 100.8 (s,1C), δ120(Q,2C); δ180.5 (Q,2C)
$^{19}$NMR (deuterobenzene): δ−77.7 (s,6F)

EXAMPLES 3 & 4 (COMPARATIVE)

To demonstrate the unexpected stabilizing effect of the silicon atom upon this system a number of experiments were conducted whereby two purely hydrocarbon based olefins of comparable size, molecular geometry and boiling point to TMVS were effectively reacted with $Cu^{+1}$hfac and the stability/volatility of the resultant compounds determined. These two olefins were 3,3-dimethyl-1-butene (i.e. DMB) and 4.4-dimethyl-1-pentene (i.e. DMP). boiling points 41° C. and 70°-72° C. respectively. They were selected to mimic the size and shape of TMVS and to span its boiling point.

Mixing potassium hfac with DMB in the presence of cuprous chloride in hexane solvent under ambient conditions resulted in no reaction. The same reactants mixed together under the same conditions in THF lead to the production of copper metal and a yellow-brown solution. Filtration of solids followed by the evaporation of THF yielded a brown sludge-like solid. $^1H$ NMR of ths solid indicated that it was not the desired product. An attempted sublimation of this material yielded only $Cu^{+2}(hfac)_2$, the latter identified by infrared spectroscopy. In the reaction between H(hfac). cuprous oxide and DMB in THF. extensive disproportionation occured and NMR analysis of the remainder of the reaction product indicated that the desired complex had not formed. An attempted sublimation of this reaction mixture to potentially liberate any volatile $Cu^{+1}$ complex only resulted in the the isolation of $Cu^{+2}(hfac)_2$ as identified by infrared spectroscopy.

Mixing potassium hfac with DMP in the presence of cuprous chloride in hexane solvent under ambient conditions resulted in the isolation of a few drops of pale yellow liquid, NMR of which could not be assigned to that of the desired product. Sublimation of this liquid at 45°-50° C. liberated a yellow -green oil, $^1H$ NMR of which indicated it to not be the desired product. Reacting together potassium hfac with DMP in the presence of cuprous chloride in THF solvent under ambient conditions led to precipitation of copper and a yellow brown solution, as in the case of DMB. Filtration of the reaction mixture and evaporation of the THF gave a brown solid. $^1H$ NMR of this solid indicated it to not be the desired complex. Under conditions suitable for the sublimation of $Cu^{+2}(hfac)_2$ no volatiles were observed to be liberated from this solid. Subliming at $>200°$ C. led only to the formation of $Cu^{+2}(hfac)_2$, identified by infrared spectroscopy. Treating H(hfac) ligand with cuprous oxide in the presence of DMP in THF lead to the formation of a green-brown solid containing copper metal. $^1H$ NMR of this solid indicates it to not be the desired product. Sublimation of this solid yielded $Cu^{+2}(hfac)_2$.

EXAMPLES 5 & 6 (COMPARATIVE)

Additional experiments were also conducted using two simple linear olefins, i.e. 1-hexene {i.e. HX}and 1-tridecene (i.e. TD), boiling points 62°-64° C. and 232° C., respectively. The latter olefin was used since its low volatility was anticipated to suppress disproportionation of the resultant complex under ambient conditions, as generally reported by Doyle.

Reacting together potassium hfac with 1-hexene and cuprous chloride in THF led to a yellow solution containing copper particles. These were filtered and the THF evaporated. This led to the production of further copper. Attempted distillation of the resulting yellow slurry yielded $Cu^{+2}(hfac)_2$ and a pale green distillate. $^1H$ NMR of which indicated it to not be the desired complex. The same reaction, only run in hexane yielded a pale green solution contaminated with copper particles. Filtration and evaporation of hexane yielded a turbid green-yellow oil, the $^1HNMR$ of which was inconsistent with that of the desired product. Upon standing in an inert atmosphere this slowly degraded to yield copper metal. Reacting cuprous oxide with H(hfac}and 1-hexene in THF lead to a dark green green solution and a precipitate of copper spheres of approx 1-2 mm in diameter. Evaporation of THF yielded a green brown paste, $^1H$ NMR of which was inconsistent with that of the desired product. Sublimation at 50°-60° C. $10^{-3}$ torr yielded mostly $Cu^{+2}(hfac)_2$.

Reacting together TD with potassium hfac and cuprous chloride in either THF or hexane under ambient conditions resulted in mixture of a liquid complex of the formula $Cu^{+1}hfac.TD$ and unreacted TD. By vacuum distillation these two compounds were separated. However, when it was attempted to distill the liquid complex complete decomposition occured to yield $Cu^{+2}(hfac)_2$. TD and copper metal, i.e. a disproportionation occured. Treatment of cuprous oxide with hfac ligand and TD in THF also yielded similar results.

Summarizing the results of Examples 1-6 above, it can be seen that in all the above syntheses, silylolefin compounds were found to yield isolable and characterizable volatile liquid compounds. For the $CuCl/K^+(hfac)^-$/silylolefin reactions in either THF or hexane no copper metal or $Cu^{+2}(hfac)_2$ was seen to form and the desired compounds could be isolated as volatile liquids. In the hydrocarbon systems, copper metal and $Cu^{+2}(hfac)_2$ would typically form in abundance under identical conditions (from the disproportionation of metastable $Cu^{+1}$ compounds as they formed) and all of the hydrocarbon olefin reactions failed to yield the desired stable $copper^{+1}$ compounds as isolable identifiable volatile materials. From these preparations it was concluded that silylated olefins such as TMVS provide stable complex(es) when coordinated to $Cu^{+1}hfac$ whereas coordination of comparable hydrocarbons DMB, DMP and 1-hexene does not provide stable complexes. Similarly, TD olefin did not yield a complex that is stable towards sublimation. These results clearly indicate the unexpected stabilizing influence of silicon in the $Cu^{+1}hfac.TMVS$ series of compounds and proves that these new silicon containing complexes are chemically distinct from those compounds described by Doyle. It is believed that in order to obtain stable volatile $Cu^{+1}$ complexes using volatile hydrocarbons such as DMB, DMP and 1-hexene, superatmospheric pressures of olefin and/or lower temperatures would be required. The less volatile TD, while forming a $Cu^{+1}hfac$ complex, would also require an elevated pressure of olefin and/or lower temperature to volatize without decomposition. While these compounds could be made under these conditions, they would not be suitable as precursors in the atmospheric pressure or LPCVD processes used by the electronic device fabrication industry

EXAMPLE 7 (COMPARATIVE)

Additional runs were carried out in an attempt to prepare the $Cu^{+1}$ hfac complex of allyltrimethylsilane wherein the silicon atom is not directly attached to an olefinic double bond as in the present compounds, but rather is attached via a methylene group. These runs were carried out under the same conditions as those utilized in the synthesis of $Cu^{+1}(hfac).TMVS$ as described above. No volatile liquid or solid complex was obtained from these runs, thus indicating the uniqueness of the stabilizing effect of silicon in the presently claimed compounds. Additionally these runs give a strong indication that olefinic molecules which simply contain a silicon group not directly attached to the olefinic double bond do not stabilize $Cu^{+1}(hfac)$ as effectively as those in which silicon is directly attached to the double bond.

EXAMPLE 8 (COMPARATIVE)

Several runs were carried out under the same conditions as those utilized for the synthesis of $Cu^{+1}(hfac).TMVS$ described above except that in one run acetylacetonate, and in another run trifluoroacetylacetonate, were substituted for the β-diketonates of the present invention. Neither of these runs produced stable volatile liquid complexes, thus demonstrating the necessity of the perfluoroalkyl β-diketonate anion in these type of compounds.

EXAMPLES 9-25

The selectivity of deposition from these silylolefin stabilized $Cu^{+1}(hfac)$ compounds was demonstrated using $Cu^{+1}(hfac).TMVS$ in two different ways. In one set of experiments a metallized silicon coupon, for example tungsten on silicon, was set alongside another silicon coupon bearing a silicon oxide surface and the two samples are simultaneously exposed to the same CVD conditions for the deposition of copper. In each case a strong selectivity towards the metallic surface was observed in the form of an adherent thick copper film forming upon it compared to little or no copper deposition on the silicon oxide. In the other set of experiments, selectivity was demonstrated by exposing a metallic/silicon oxide "patterned wafer" or FLTC {Fine Line Test Circuit}to copper CVD conditions whereupon it was observed that copper deposition occurred only on the metallic surface and not on the silicon oxide. Compared to the first set of experiments where macroscopic selectivity is demonstrated between relatively large juxtaposed surfaces, the FLTC experiments show selectivity on a microscopic scale that is significantly more closely akin to actual IC manufacturing conditions that would be used to fabricate metallic interconnects via CVD. That is, observation was made of selective deposition of copper onto metallic surfaces that are approximately 2 microns wide separated by approximately 2 microns of silicon oxide. Macroscopic selectivity, however, was found to be in general agreement with that observed for the patterned wafers hence making the macroscopic results a strong predictive tool for FLTC experiments. Thus selective deposition of copper was observed onto "bulk surfaces" of tantalum and titanium nitride versus silicon oxide in addition to the selective depositions observed using the above tungsten/silicon oxide FLTC. Selectivity was determined by both visual inspection of the coupons at 200-1000× using an optical microscope and by a scanning electron microscope (SEM) to determine the presence or absence of copper. The thickness of each deposited film in Runs 9-18 was determined by viewing them edge on in SEM. The thickness of the copper films in Examples 12-16 was determined by etching part of the copper film from the TiN surface using nitric acid then tracking across the TiN/copper boundary using a stylus profilometer to measure the copper film thickness. Copper grain size was also directly measured from SEM photographs. Inspection of these SEM photographs clearly indicated excellent selective deposition of copper onto H, TiN, or Ta. All of the films were found to be highly adherent by their resisting being lifted from their substrate surfaces by the application and subsequent removal of 3M ® Scotch tape. AES depth profiling indicated the copper films to be >99.9% pure copper (ie. O, F, C, below detectable limits) for Examples 12, 19, and 25. The resistivity of the deposited copper was determined to be 1.9-2.2 microohm cm.

The depositions were carried out as follows for Examples 9-17: Vapors of pure $Cu^{+1}$(hfac).TMVS were fed into a four-way vacuum cross of a cold wall CVD reactor by means of a dynamic vacuum of approx $10^{-1}$ torr where they contacted a resistively heated stainless steel susceptor bearing the sample coupons set at the predetermined deposition temperature. The actual temperature of a given sample was measured via a thermocouple contacting the underside of the test coupon. Each run would start by first loading the test coupons onto the susceptor under a purge of nitrogen and evacuating the reactor to $10^{-6}$ torr for 30 minutes whilst heating the susceptor to the desired run temperature. Vapors of the silylolefin precursor were then passed through the reactor and over the susceptor. This was accomplished by connecting a sealed source of the precursor under its own vapor pressure upstream to the four-way cross, pumping out the sysyem and then opening the source seal thereby allowing precursor vapors to flow through the reactor under a dynamic vacuum of approximately $10^{-1}$ torr. A liquid nitrogen cooling trap positioned upstream of the pump condensed out all the volatiles from the CVD process. During these runs unreacted copper$^{(+1)}$ complex was observed in the trap as a yellow green oil along with dark blue crystals of $Cu^{+2}$(hfac)$_2$ as a product of disproportionation. The source vessel bearing the complex was water bath heated to 40° C. and the delivery lines from it to the susceptor and the reactor walls were both heat traced to 60° C. Alternatively, the silylolefin precursor could be run through the reactor by bubbling argon gas through it at an overall reactor pressure of 10-20 torr (Examples 18 & 20-24). In this way copper was selectively deposited onto the tungsten portion of an FLTC coupon at 150° C. (run 18) and onto TiN between 150° and 350° C. (Examples 20-24). In the latter cases only coupons of TiN were used therefore selectivity is not reported.

For the 0.1 torr Examples 9-17 using the FLTCs selective deposition of copper was observed between 120° C. and 420° C. In all Examples the precursor used was $Cu^{+1}$(hfac).TMVS. The conditions used and results of these runs are listed in Table 1 below. The results reported in this Table clearly show that selective deposition of copper onto metallic substrates can be achieved using the organometallic copper precursors of the claimed invention.

TABLE 1

| Example | Source Temperature °C. | Total System Pressure (torr) | Substrates | Substrate Temperature °C. | Selectivity | Film Thickness (nm) | Grain Size (nm) | Growth Rate (nm/min) |
|---|---|---|---|---|---|---|---|---|
| 9 | 40 | 0.1 | W$^{(a)}$ vs. SiO$_2^{(a)}$ | 150 | W | 200 | 50-75 | 13 |
| 10 | 40 | 0.1 | W$^{(a)}$ vs. SiO$_2^{(a)}$ | 180 | W | 200 | 150 | 13 |
| 11 | 40 | 0.1 | W$^{(a)}$ vs. SiO$_2^{(a)}$ | 210 | W | 250 | 175-200 | 12.5 |
| 12 | 40 | 0.1 | W$^{(a)}$ vs. SiO$_2^{(a)}$ | 240 | W | 200 | 250-350 | 9 |
| 13 | 40 | 0.1 | W$^{(a)}$ vs. SiO$_2^{(a)}$ | 270 | W | 200 | 250-350 | 10 |
| 14 | 40 | 0.1 | W$^{(a)}$ vs. SiO$_2^{(a)}$ | 300 | W | 200 | 250-700 | 10 |
| 15 | 40 | 0.1 | W$^{(a)}$ vs. SiO$_2^{(a)}$ | 360 | W | 200 | 500-700 | 50 |
| 16 | 40 | 0.1 | W$^{(a)}$ vs. SiO$_2^{(a)}$ | 390 | W | 300 | 300-700 | 120 |
| 17 | 40 | 0.1 | W$^{(a)}$ vs. SiO$_2^{(a)}$ | 420 | W | 200 | 300-600 | 200 |
| 18 | 40 | 20(Ar)$^{(e)}$ | W$^{(a)}$ vs. SiO$_2^{(a)}$ | 150 | W | N/A | N/A | N/A |
| 19 | 40 | | TiN$^{(b)}$ vs. SiO$_2^{(c)}$ | 180 | TiN | 33 | N/A | 2.0 |
| 20 | 40 | 10(Ar)$^{(e)}$ | TiN$^{(b)}$ | 150 | TiN | 360 | 165 | 14.4 |
| 21 | 40 | 10(Ar)$^{(e)}$ | TiN$^{(b)}$ | 200 | TiN | 410 | 200 | 20.5 |
| 22 | 40 | 10(Ar)$^{(e)}$ | TiN$^{(b)}$ | 250 | TiN | 450 | 470 | 22.5 |
| 23 | 40 | 10(Ar)$^{(e)}$ | TiN$^{(b)}$ | 300 | TiN | 490 | 590 | 24.5 |
| 24 | 40 | 10(Ar)$^{(e)}$ | TiN$^{(b)}$ | 350 | TiN | 590 | 650 | 29.5 |

TABLE 1-continued

| Example | Source Temperature °C. | Total System Pressure (torr) | Substrates | Substrate Temperature °C. | Selectivity | Film Thickness (nm) | Grain Size (nm) | Growth Rate (nm/min) |
|---|---|---|---|---|---|---|---|---|
| 25 | 40 | | Ta$^{(d)}$ vs. SiO$_2$$^{(c)}$ | 180 | Ta | 136 | N/A | 3.0 |

In all runs reactor walls and delivery lines = 60° C.
$^{(a)}$W/SiO$_2$ FLTC prepared by CVD deposition of ~200 Å of W onto a silicon oxide/silicon trench patterned wafer.
$^{(b)}$TiN 550 Å thick layer applied by reactive ion sputtering onto a silicon 100 wafer.
$^{(c)}$SiO$_2$ grown by CVD onto Si(100) wafer using tetraethoxysilane precursor.
$^{(d)}$Ta 1200 Å thick layer applied by magnetron sputtering onto 500 Å of silicon oxide thermally grown onto a Si 100 wafer.
$^{(e)}$Flow of argon through Cu$^{+1}$(hfac)·TMVS source was 9.2 SCCM.
$^{(f)}$N/A = values not measured.

EXAMPLE 26

Runs were carried out to demonstrate that the CVD reaction of the present invention could be reversed to selectively etch deposited copper metal from the surface of a substrate using a mixture of Cu$^{+2}$(hfac)$_2$ and an appropriate silylolefin, both in the vapor phase. A stream of argon gas a flow rate of 122 sccm and a pressure of 200 torr was bubbled through a sample of Cu$^{+2}$(hfac)$_2$ (molten at 100° C.) to yield a saturated vapor of the copper complex. A separate stream of argon at a flow rate of 122 sccm and 200 torr pressure was bubbled through a sample of TMVS at 0° C. to yield a saturated vapor of TMVS. These two gas streams were then mixed to yield an atmosphere composed of approximately 100 torr TMVS, 10 torr Cu$^{+2}$(hfac)$_2$ and 90 torr argon. This gaseous mixture was then passed over a copper covered surface heated to 140° C. for 15 minutes resulting in an etching of the copper surface. In separate experiments, identical copper surfaces at 140° C. were exposed to either pure Cu$^{+2}$(hfac)$_2$ vapors (10 torr copper complex in argon at a total pressure of 200 torr) or to pure TMVS vapor (100 torr in argon at a total pressure of 200 torr) at flow rates of 122 sccm in each case. Neither of these runs resulted in any observable etching of copper. Thus, the necessity of requiring both components in unison to accomplish the etch was demonstrated. The etched sample was a silicon coupon that had been covered sequentially with 5000Å of silicon oxide 1200Å of tantalum and 1000Å of copper. The surface of the coupon was partially masked with polyimide tape such that only a narrow trench of copper was exposed to the etch vapors. Once the etch was completed, the tape was removed and the extent of the etch determined by measuring the depth of copper removed from the surface via a stylus profilometer. In this technique, a sapphire stylus point contacts and tracks across the surface of the etched coupon and directly measures its surface topography in units of Angstroms.

What is claimed is:

1. A process for selectively depositing a copper metal film by chemical vapor deposition onto a metallic or other electrically conducting portion of a substrate surface, said process comprising contacting a substrate having a surface of which a portion comprises a metallic or electrically conducting material with a volatile organometallic copper complex under chemical vapor deposition conditions, said organometallic copper complex being represented by the structural formula:

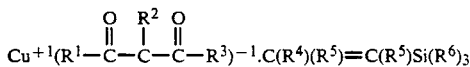

wherein R$^1$ and R$^3$ are each independently C$_1$-C$_8$ perfluoroalkyl, R$^2$ is H, F or C$_1$-C$_8$ perfluoroalkyl, R$^4$ is H, C$_1$-C$_8$ alkyl, or Si(R$^6$)$_3$, each R$^5$ is independently H or C$_1$-C$_8$ alkyl and each R$^6$ is independently phenyl or C$_1$-C$_8$ alkyl.

2. The process of claim 1 wherein each R$^5$ is H.

3. The process of claim 2 wherein R$^4$ is H.

4. The process of claim 3 wherein R$^6$ is a methyl group.

5. The process of claim 1 wherein R$^2$ is H.

6. The process of claim 5 wherein both R$^1$ and R$^3$ are CF$_3$.

7. The process of claim 1 wherein the surface onto which the copper metal film is deposited is selected from the group consisting of: W, TiN, Ta, and Al.

8. The process of claim 1 wherein the deposition temperature is from 120° C. to 200° C.

9. The process of claim 1 wherein said substrate is contacted with hydrogen gas along with the organometallic precursor.

10. A process for selectively etching a copper film from the surface of a substrate, said process comprising:
contacting the substrate having a copper film surface with an organometallic copper complex and a silylolefin ligand, both in the gas phase, wherein said complex and said silylolefin ligand are represented by the structural formulae:

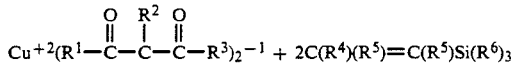

wherein R$^1$ and R$^3$ are each independently C$_1$-C$_8$ perfluoroalkyl, R2 is H, F or C$_1$-C$_8$ perfluoroalkyl, R$^4$ is H, C$_1$-C$_8$ alkyl, or Si(R$^6$)$_3$, each R$_5$ is independently H or C$_1$-C$_8$ alkyl and each R$_6$ is independently phenyl or C$_1$-C$_8$ alkyl.

11. The process of claim 10 wherein the organometallic copper complex is Cu$^{+2}$(hexafluoroacetylacetonate$^{31}$ $^1$)$_2$ and the silylolefin is trimethylvinylsilane.

* * * * *

UNITED STATES PATENT AND TRADEMARK OFFICE
CERTIFICATE OF CORRECTION

PATENT NO. : 5,085,731
DATED : February 4, 1992
INVENTOR(S) : John A. T. Norman, et al It is certified that error appears in the above-identified patent and that said Letters Patent is hereby corrected as shown below:

Column 14, Line 59

Delete "$3^1$ $^1)$" and substitute therefore -- $^{-1})$ --

Signed and Sealed this

Second Day of November, 1993

Attest:

BRUCE LEHMAN

Attesting Officer    Commissioner of Patents and Trademarks